United States Patent

Nagano et al.

[11] Patent Number: 4,880,925
[45] Date of Patent: Nov. 14, 1989

[54] INTERMEDIATES FOR THE PRODUCTION OF TETRAHYDROPHTHALIMIDES

[75] Inventors: Eiki Nagano, Nishinomiya; Toru Haga, Takarazuka; Ryo Sato; Kouichi Morita, both of Toyonaka, all of Japan

[73] Assignee: Sumitomo Chemical Company, Ltd., Osaka, Japan

[21] Appl. No.: 246,783

[22] Filed: Sep. 20, 1988

Related U.S. Application Data

[62] Division of Ser. No. 914,496, Oct. 2, 1986, Pat. No. 4,772,605, which is a division of Ser. No. 756,251, Jul. 18, 1985, Pat. No. 4,640,707.

[30] Foreign Application Priority Data

Jul. 23, 1984 [JP] Japan .................. 59-152721
Aug. 3, 1984 [JP] Japan .................. 59-164020
Sep. 20, 1984 [JP] Japan .................. 59-198245

[51] Int. Cl.$^4$ .......................... C07D 265/36
[52] U.S. Cl. .................................. 544/105
[58] Field of Search ........................ 544/105

[56] References Cited

U.S. PATENT DOCUMENTS 3,733,321  5/1973  Krapcho ............. 544/105 X

FOREIGN PATENT DOCUMENTS 16882  1/1984  Japan .

OTHER PUBLICATIONS

Coutts et al, Chemical Abstracts, vol. 73 (1970) 35305n.
Matschiner et al, Chemical Abstracts, vol. 96 (1982) 142783p.
Hashimoto et al, Chemical Abstracts, vol. 100 (1984) 138358n.

Primary Examiner—Richard L. Raymond
Attorney, Agent, or Firm—Birch, Stewart, Kolasch & Birch

[57] ABSTRACT

A compound of the formula:

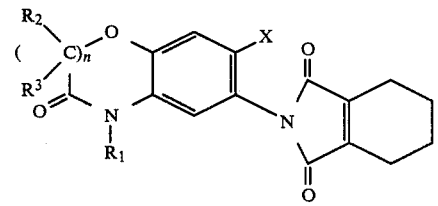

wherein $R_1$ is a hydrogen atom, a $C_1$–$C_5$ alkyl group, a $C_3$–$C_4$ alkenyl group, a $C_3$–$C_4$ alkynyl group, a $C_1$–$C_4$ haloalkyl group, a $C_3$–$C_4$ haloalkenyl group, a $C_3$–$C_4$ haloalkynyl group, a $C_1$–$C_2$ alkoxy($C_1$–$C_2$)alkyl group or a $C_1$–$C_2$ alkoxy($C_1$–$C_2$)alkoxy($C_1$–$C_2$)alkyl group, $R_2$ and $R_3$ are, the same or different, each a hydrogen atom, a halogen atom, a $C_1$–$C_3$ alkyl group or a phenyl group, X is a hydrogen atom, a chlorine atom or a fluorine atom and n is an integer of 0 or 1, which is useful as a herbicide.

3 Claims, No Drawings

INTERMEDIATES FOR THE PRODUCTION OF TETRAHYDROPHTHALIMIDES

This application is a divisional of copending application Ser. No. 914,496, filed on Oct. 2, 1986, now U.S. Pat. No. 4,772,605 which in turn was a divisional of application Ser. No. 756,251 filed July 18, 1985, U.S. Pat. No. 4,640,707.

This invention relates to tetrahydrophthalimides, and their production and use. More particularly, it relates to tetrahydrophthalimides of the formula:

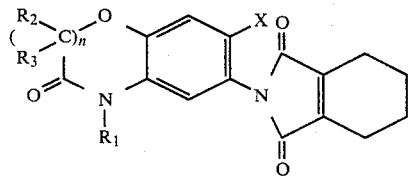

wherein $R_1$ is a hydrogen atom, a $C_1$–$C_5$ alkyl group, a $C_3$–$C_4$ alkenyl group, a $C_3$–$C_4$ alkynyl group, a $C_1$–$C_4$ haloalkyl group, a $C_3$–$C_4$ haloalkenyl group, a $C_3$–$C_4$ haloalkynyl group, a $C_1$–$C_2$ alkoxy($C_1$–$C_2$)alkyl group or a $C_1$–$C_2$ alkoxy($C_1$–$C_2$)alkoxy($C_1$–$C_2$)alkyl group, $R_2$ and $R_3$ are the same or different, each a hydrogen atom, a halogen atom, a $C_1$–$C_3$ alkyl group or a phenyl group, X is a hydrogen atom, a chlorine atom or a fluorine atom and n is an integer of 0 or 1, and their production and use.

The term "halogen" used herein includes chlorine, bromine and fluorine.

It is known that certain kinds of tetrahydrophthalimides are useful as herbicides. For instance, the herbicidal use of 2-(4-methoxyphenyl)-4,5,6,7-tetrahydro-2H-isoindole-1,3-dione is disclosed in U.S. Pat. No. 3,878,224. However, their herbicidal effect is not always satisfactory.

It has been found that the tetrahydrophthalimides (I) show a high herbicidal activity against a wide variety of weeds including broad-leaved weeds, Graminaceous weeds, Commelinaceous weeds and Cyperaceous weeds in agricultural plowed field by foliar or soil treatment without producing any material phytotoxicity on various agricultural crops such as wheat, barley, corn, soybean and peanut. Examples of broad-leaved weeds are wild buckwheat (*Polygonum convolvulus*), ladysthumb (*Polygonum persicaria*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), ivyleaf morningglory (*Ipomoea hederacea*), tall morningglory (*Ipomoea purpurea*), henbit (*Laminum amplexicaure*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforate*), pineappleweed (*Matricaria matricarioides*), oxeye daisy (*Chrysanthemum leucanthemum*), corn marigold (*Chrysanthemum segetum*), sun spurge (*Euphorbia helioscopia*), etc. Examples of Graminaceous weeds are Japanese millet (*Echinochloa frumentacea*), barnyardgrass (*Echinochloa crusgalli*), sicklepod (*Cassia obtusifolia*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), etc. Examples of Commelinaceous weeds are asiatic dayflower (*Commelina communis*), etc. Examples of Cyperaceous weeds are yellow nutsedge (*Cyperus esculentus*), etc.

On the pre-emergence soil treatment, the tetrahydrophthalimides (I) exhibit a particularly strong herbicidal activity against broad-leaved weeds such as catchweed bedstraw, common chickweed, field pansy, persian speedwell, scentless chamomile, pale smartweed, ladysthumb, wild mustard, pineappleweed, oxeye daisy, common lambsquarters, black nightshade, field bindweed and redroot pigweed in the field of wheat or barley while exerting no or little chemical injury to wheat or barley; they also exhibit a marked herbicidal activity against broad-leaved weeds such as velvetleaf, common cocklebur, tall morningglory, sicklepod, prickly sida, jimsonweed, hemp sesbania, redroot pigweed, common lambsquarters and black nightshade in the field of soybean or peanut while exerting no or little chemical injury to soybean or peanut.

Further, some of the tetrahydrophthalimides (I) of the invention are effective in exterminating the paddy field weeds including Graminaceous weeds such as barnyardgrass (*Echinochloa oryzicola*) and broad-leaved weed such as common falsepimpernel (*Lindernia procumbens*), indian toothcup (*Rotala indica*) and waterwort (*Elatine triandra*) without any phytotoxicity to rice plants on flooding treatment.

Among the tetrahydrophthalimides (I), those wherein X is a hydrogen atom or a fluorine atom are preferred. More preferred are those wherein $R_1$ is a $C_1$–$C_4$ alkyl group, a $C_3$–$C_4$ alkenyl group, a $C_3$–$C_4$ alkynyl group, a $C_3$–$C_4$ haloalkynyl group or a $C_1$–$C_2$ alkoxymethyl group and $R_2$ and $R_3$ are each a hydrogen atom, a methyl group or an ethyl group. Much more preferred are those wherein $R_1$ is a $C_1$–$C_3$ alkyl group, a $C_3$–$C_4$ alkenyl group, a $C_3$–$C_4$ alkynyl group or a halopropynyl group, especially n is an integer of 1. Most preferred ae those wherein $R_2$ is a hydrogen atom or a methyl group and $R_3$ is a hydrogen atom, especially when $R_1$ is a $C_3$–$C_4$ alkenyl group or a $C_3$–$C_4$ alkynyl group. Specific examples are 2-[4-(2-propynyl)-2H-1,4-benzoxazin-3(4H)-on-6-yl]-4,5,6,7-tetrahydro-2H-isoindole-1,3-dione, 2-[2-methyl-4-(2-propynyl)-2H-1,4-benzoxazin-3(4H)-on-6-yl]-4,5,6,7-tetrahydro-2H-isoindole-1,3-dione, 2-[7-fluoro-4-(2-propynyl)-2H-1,4-benzoxazin-3(4H)-on-6-yl]-4,5,6,7-tetrahydro-2H-isoindole-1,3-dione, 2-[7-fluoro-2-methyl-4-(2-propynyl)-2H-1,4-benzoxazin-3(4H)-on-6-yl]-4,5,6,7-tetrahydro-2H-isoindole-1,3-dione, etc.

The tetrahydrophthalimides (I) of the invention are obtainable by reacting an amino compound of the formula:

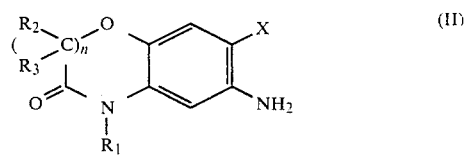

wherein $R_1$, $R_2$, $R_3$, X and n are each as defined above with a 3,4,5,6-tetrahydrophthalic anhydride in a solvent at a temperature of 80° to 200° C. for a period of 1 to 24 hours. In the reaction, the 3,4,5,6-tetrahydrophthalic anhydride is used in an amount of 1 to 3 equivalents to 1 equivalent of the amino compound (II). Examples of the solvent are aliphatic hydrocarbons (e.g. hexane, heptane, ligroin), aromatic hydrocarbons (e.g. benzene, toluene, xylene), ethers (e.g. diisopropyl ether, dioxane, ethylene glycol dimethyl ether), fatty acids (e.g. formic acid, acetic acid, propionic acid), water, and mixtures thereof.

After completion of the reaction, the reaction mixture is subjected to ordinary post-treatment. For instance, the reaction mixture is, if necessary, admixed with water, and the precipitated crystals are collected by filtration. Alternatively, the reaction mixture is optionally admixed with water, followed by solvent extraction or concentration. Further, if necessary, the purification by chromatography or recrystallization may be applied.

Practical and presently preferred embodiments for production of the tetrahydrophthalimides (I) are illustratively shown in the following Examples.

EXAMPLE 1

A mixture of 6-amino-4-(2-propynyl)-2H-1,4-benzoxazin-3(4H)-one (0.8 g), 3,4,5,6-tetrahydrophthalic anhydride (0.61 g) and acetic acid (20 ml) was heated under reflux for 2 hours. After being allowed to cool, water was added to the mixture, and the precipitated crystals were collected by filtration and washed with water. Recrystallization from ethanol gave 2-[4-(2-propynyl)-2H-1,4-benzoxazin-3(4H)-on-6-yl]-4,5,6,7-tetrahydro-2H-isoindole-1,3-dione (0.4 g). m.p., 205°–206° C.

$^1$H-NHR (CDCl$_3$) δ ppm: 1.8 (4H, m), 2.2 (1H, t), 2.4 (4H, m), 4.6 (2H, s), 4.62 (2H, d), 7.0–7.3 (3H, m).

EXAMPLE 2

A mixture of 6-amino-7-fluoro-4-(2-propynyl)-2H-1,4-benzoxazin-3(4H)-one (0.31 g), 3,4,5,6-tetrahydrophthalic anhydride (0.28 g) and acetic acid (3 ml) was heated under reflux for 2 hours. After being allowed to cool, water was added to the mixture, which was then extracted with ethyl acetate. The organic layer was washed with water, neutralized with sodium bicarbonate solution, dried and concentrated. The residue was purified by silica gel thin layer chromatography using a mixture of ethyl acetate and hexane (1:2) as an eluent to give 2-[7-fluoro-4-(2-propynyl)-2H-1,4-benzoxazin-3(4H)-on-6-yl]-4,5,6,7-tetrahydro-2H-isoindole-1,3-dione (0.12 ). m.p., 196.0° C.

$^1$H-NHR (CDCl$_3$) δ ppm: 1.81 (4H, m), 2.4 (4H, m), 2.53 (1H, t), 4.62 (2H, s), 4.73 (2H, d), 6.88 (1H, d, J=10 Hz), 7.04 (1H, d, J=6 Hz).

EXAMPLE 3

A mixture of 5-amino-3-(2-propynyl)-3H-benzoxazol-2-one (0.50 g), 3,4,5,6-tetrahydrophthalic anhydride (0.53 g) and acetic acid (5 ml) was heated at 100° to 110° C. under reflux for 3 hours. After being allowed to cool, water was added to the mixture, which was then extracted with ethyl acetate. The organic layer was washed with water, neutralized with sodium bicarbonate solution, dried and concentrated to give 2-[3-(2-propynyl)-3H-benzoxazol-2-on-5-yl]-4,5,6,7-tetrahydro-2H-isoindole-1,3-dione (0.30 g). m.p., 285.5° C.

$^1$H-NHR (CDCl$_3$) δ ppm: 1.8 (4H, m), 2.22 (1H, t), 2.4 (4H, m), 4.60 (2H, d), 7.0–7.3 (3H, m).

In the same manner as above, the tetrahydrophthalimides (I) as shown in Table 1 were obtained.

TABLE 1

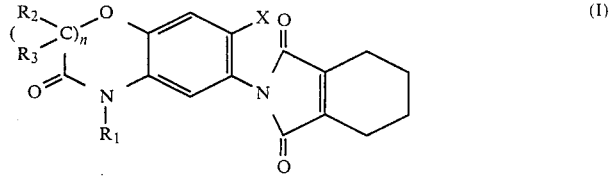

(I)

| Compound No. | n | $R_1$ | $R_2$ | $R_3$ | X | Physical constant |
|---|---|---|---|---|---|---|
| 1 | 0 | CH≡CCH$_2$— | | | H | m.p. 285.5° C. |
| 2 | 0 | CH≡CCH$_2$— | | | F | m.p. 194–196° C. |
| 3 | 0 | CH$_2$=CHCH$_2$— | | | H | m.p. 142–143° C. |
| 4 | 0 | n-C$_3$H$_7$ | | | H | m.p. 131–132° C. |
| 5 | 0 | C$_2$H$_5$ | | | H | m.p. 150–151° C. |
| 6 | 1 | H | H | H | H | m.p. 240–241° C. |
| 7 | 1 | H | H | H | F | m.p. 233.0° C. |
| 8 | 1 | CH$_3$ | H | H | H | m.p. 121–123° C. |
| 9 | 1 | C$_2$H$_5$ | H | H | H | m.p. 149.5–151° C. |
| 10 | 1 | n-C$_3$H$_7$ | H | H | H | m.p. 127–128.5° C. |
| 11 | 1 | n-C$_4$H$_9$ | H | H | H | m.p. 147–148° C. |
| 12 | 1 | i-C$_4$H$_9$ | H | H | H | m.p. 150–151° C. |
| 13 | 1 | i-C$_5$H$_{11}$ | H | H | H | glassy |
| 14 | 1 | CH$_2$=CHCH$_2$— | H | H | H | m.p. 167–168.5° C. |
| 15 | 1 | CH≡CCH$_2$— | H | H | H | m.p. 205–206° C. |
| 16 | 1 | CH≡CCH$_2$— | CH$_3$ | H | H | m.p. 167.5–168° C. |
| 17 | 1 | CH$_3$OCH$_2$— | H | H | H | m.p. 150–151° C. |
| 18 | 1 | C$_2$H$_5$OCH$_2$— | H | H | H | m.p. 139–140.5° C. |
| 19 | 1 | CH$_3$OCH$_2$CH$_2$OCH$_2$— | H | H | H | m.p. 142–143° C. |
| 20 | 1 | CH≡CCH$_2$— | H | H | F | m.p. 196.0° C. |
| 21 | 1 | C$_2$H$_5$ | H | H | F | m.p. 173–174° C. |
| 22 | 1 | CH$_2$=CHCH$_2$— | H | H | F | m.p. 167.9° C. |
| 23 | 1 | C$_2$H$_5$OCH$_2$— | H | H | F | m.p. 173–174° C. |
| 24 | 1 | n-C$_3$H$_7$ | H | H | F | m.p. 144.5° C. |
| 25 | 1 | CH≡CCH$_2$— | CH$_3$ | H | F | m.p. 161.5–163.5° C. |

TABLE 1-continued (I) Structure: R₂R₃C(n)-CH₂-O-[benzene ring with X, substituted with N-R₁ and fused tetrahydrophthalimide group]

| Compound No. | n | R₁ | R₂ | R₃ | X | Physical constant |
|---|---|---|---|---|---|---|
| 26 | 1 | CH≡CCH₂— | $C_2H_5$ | H | H | m.p. 154.5–155.5° C. |
| 27 | 1 | CH≡CCH₂— | $C_2H_5$ | H | F | m.p. 131–133° C. |
| 28 | 1 | CH≡CCH₂— | $CH_3$ | $CH_3$ | H | m.p 139.5–141.5° C. |
| 29 | 1 | CH≡CCH₂— | $CH_3$ | $CH_3$ | F | m.p. 88.5–90.0° C. |
| 30 | 1 | CH≡CCH₂— | n-$C_3H_7$— | H | H | $n_D^{25.5}$ 1.5691 |
| 31 | 1 | CH≡CCH₂— | n-$C_3H_7$— | H | F | $n_D^{23.5}$ 1.5410 |
| 32 | 1 | CH≡CCH₂— | n-$C_3H_7$— | H | H | $n_D^{23.5}$ 1.5491 |
| 33 | 1 | CH≡CCH₂— | H | H | Cl | m.p. 211.2° C. |
| 34 | 1 | (Z)-ClCH=C(Cl)CH₂— | H | H | H | m.p. 156–157° C. |
| 35 | 1 | (E)-ClCH=C(Cl)CH₂— | H | H | H | m.p. 155–157° C. |
| 36 | 1 | (Z)-ClCH=C(Cl)CH₂— | H | H | F | m.p. 161–162° C. |
| 37 | 1 | (E)-ClCH=C(Cl)CH₂— | H | H | F | m.p. 134.5–136.5° C. |
| 38 | 1 | $CH_2$=C(Cl)CH₂— | H | H | H | m.p. 173–173.5° C. |
| 39 | 1 | $CH_2$=C(Cl)CH₂— | H | H | F | m.p. 153–154° C. |
| 40 | 1 | ClCH₂CH=CHCH₂— | H | H | F | $n_D^{25.0}$ 1.5546 |
| 41 | 1 | CH≡CCH₂— | $C_6H_5$— | H | H | m.p. 181–182° C. |
| 42 | 1 | CH₃(Cl)C=CHCH₂— | H | H | H | $n_D^{24.5}$ 1.5870 |
| 43 | 1 | CH₃(Cl)C=CHCH₂— | H | H | F | m.p. 179–180° C. |
| 44 | 1 | ClCH=CHCH₂— | H | H | H | m.p. 119.5–121° C. |
| 45 | 1 | ClCH=CHCH₂— | H | H | F | m.p. 150–151° C. |
| 46 | 1 | Cl₂C=CHCH₂— | H | H | H | m.p. 192.5–193.5° C. |
| 47 | 1 | Cl₂C=CHCH₂— | H | H | F | m.p. 204.5–206° C. |
| 48 | 1 | BrC≡CCH₂— | H | H | H | m.p. 144.1° C. |
| 49 | 1 | BrC≡CCH₂— | H | H | F | m.p. 110–112° C. |
| 50 | 1 | CH≡CCH₂— | F | H | H | 177.5–179.5° C. |

The production of the starting amino compound (II) is summarized in the following scheme:

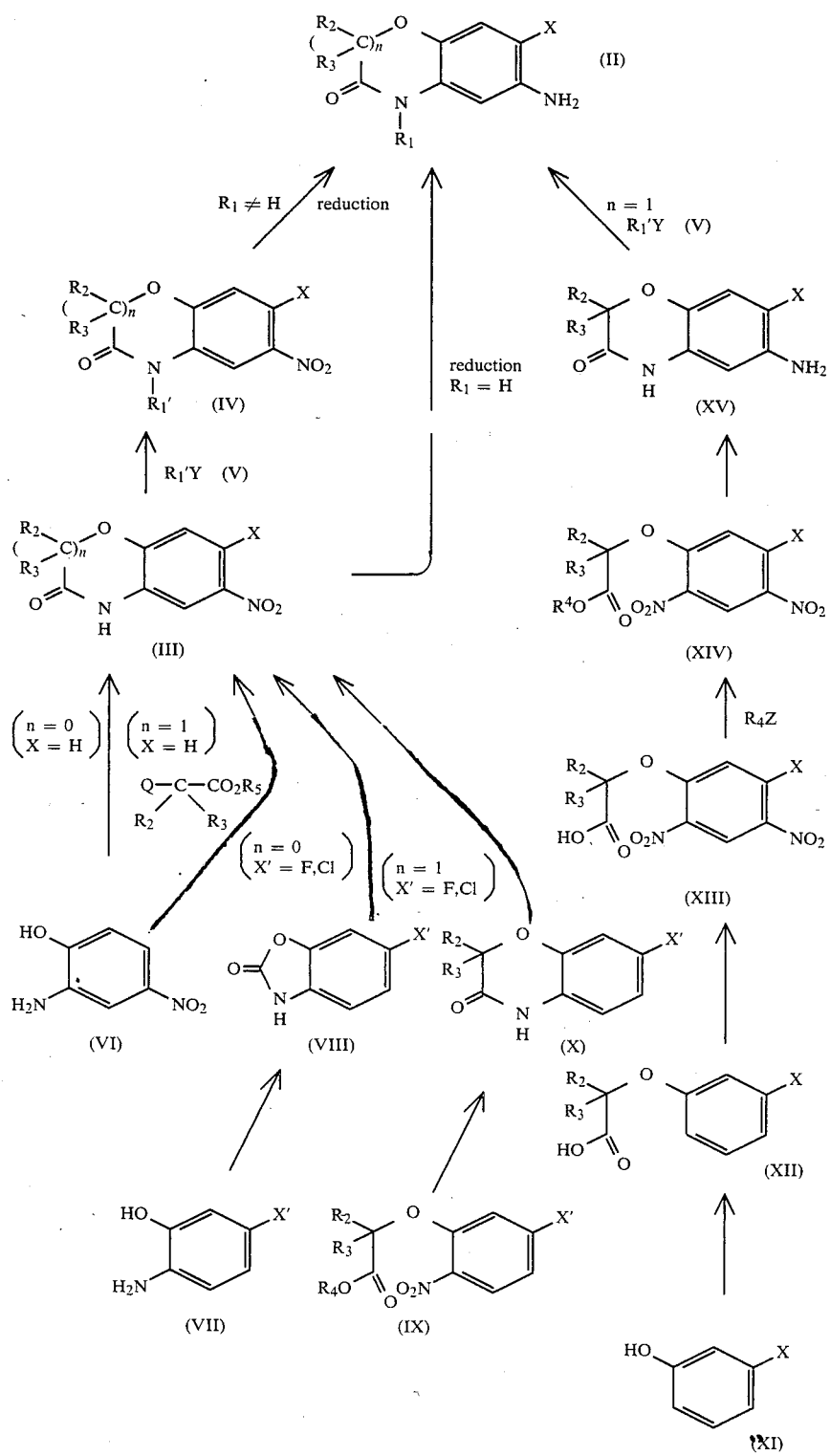

wherein $R_1$, $R_2$, $R_3$, X and n are each as defined above, X' is a fluorine atom or a chlorine atom, Y is a halogen atom, Z is a hydroxyl group, Q is a halogen atom, $R_1'$ is a $C_1$–$C_5$ alkyl group, a $C_3$–$C_4$ alkenyl group, a $C_3$–$C_4$ alkynyl group, a $C_1$–$C_4$ haloalkyl group, a $C_3$–$C_4$ haloalkenyl group, a $C_3$–$C_4$ haloalkynyl group, a $C_1$–$C_2$ alkoxy($C_1$–$C_2$)alkyl group or a $C_1$–$C_2$ alkoxy($C_1$–$C_2$)alkoxy($C_1$–$C_2$)alkyl group and $R_4$ and $R_5$ are each a lower alkyl group.

The above conversions will be explained further in detail below.

(1) Production of the compound (IV) from the compound (III)

The compound (IV) is obtainable by reacting the compound (III) with the compound (V) in a solvent in the presence of a dehydrohalogenating agent at a temperature of 0° to 80° C., preferably of 10° to 30° C. The amounts of the compound (V) and the dehydrohalogenating agent are respectively 1.0 to 1.5 and 1.0 to 1.5 equivalents to one equivalent of the compound (III). Examples of the solvent are aromatic hydrocarbons (e.g. toluene, benzene), amides (e.g. N,N-dimethylformamide), sulfur compounds (e.g. dimethylsulfoxide), nitriles (e.g. acetonitrile), water, and their mixtures. As the dehydrohalogenating agent, there may be used sodium hydride, sodium hydroxide, potassium hydroxide, etc.

After completion of the reaction, the reaction mixture is subjected to ordinary post-treatment such as addition of water, extraction with an organic solvent and concentration. If desired, any conventional purification procedure such as recrstallization or chromatography may be adopted.

(2) Production of the compound (II) from the compound (IV)

The compound (II) is obtained by reducing the compound (IV) with 2.0 to 10 equivalents of iron in the presence of an acid in a solvent (e.g. acetic acid, water, alcohol, tetrahydrofuran) at a temperature of 20° to 100° C.

After completion of the reaction, the residue is collected by filtration and extracted with an organic solvent. The extract is washed with water and sodium bicarbonate solution and concentrated. If necessary, the reaction mixture may be purified by recrystallization or chromatography as conventionally employed.

(3) Production of the compound (III)

(i) Production of the compound (III) ($n=0$; $X=H$) from the compound (VI):

The compound (III) ($n=0$; $X=H$) can be produced from the compound (VI), i.e. 2-amino-4-nitrophenol, by the method as described in J. Am. Chem. Soc., 71, 1265 (1949) and J. Pharm. Sci., 53, 538 (1964).

(ii) Production of the compound (III) ($n=1$; $X=H$) from the compound (VI):

The compound (III) ($n=1$; $X=H$) can be produced from the compound (VI), i.e. 2-amino-4-nitrophenol, by the method as described in Synthesis, 1982, 986.

(iii) Production of the compound (III) ($n=0$, $X=F$ or Cl) from the compound (VII) through the compound (VIII):

The compound (VIII) is obtainable from the compound (VII) by the method as described in J. Pharm. Sci., 53, 538 (1964), and the resultant compound (VII) is nitrated by 1.0 to 1.2 equivalents of 60% nitric acid in 80% aqeuous sulfuric acid solution at a temperature of −5° to 5° C. to give the compound (III).

(iv) Production of the compound (III) ($n=1$, $X=F$ or Cl) from the compound (IX) through the compound (X):

The compound (X) is obtained by reducing the compound (IX), which is produced by the method as described in J. Am. Chem. Soc., 81, 94 (1959), with 2.0 to 10 equivalents of iron in the presence of an acid in a solvent (e.g. acetic acid, water, alcohol, tetrahydrofuran) at a temperature of 20° to 100° C.

After completion of the reaction, the residue is collected by filtration and extracted with an organic solvent. The extract is washed with water and sodium bicarbonate solution and concentrated. If necessary, the reaction mixture may be purified by recrystallization or chromatography as conventionally employed.

The compound (X) thus obtained is subjected to nitration with a mixture of sulfuric acid and nitric acid at a temperature of −10° to 10° C. so as to selectively nitrate the 6-position of the benzoxazine ring to give the compound (III) ($n=1$; $X=F$ or Cl). Sulfuric acid and nitric acid are respectively used in amounts of one equivalent to large excess and of 1 to 1.2 equivalents to the compound (X). The concentrations of sulfuric acid and of nitric acid are preferred to be 80% and 60%, respectively.

After completion of the reaction, the reaction mixture is poured into ice water, and the precipitated crystals are collected by filtration and washed with water. If necessary, any purification method such as recrystallization or chromatography may be adopted.

(4) Production of the compound (XII) from the compound (IX)

The compound (XII) is obtainable from the compound (XI) by the method as described in Rec. Trav. Chim., 76, 128 (1957) and J. Am. Chem. Soc., 65, 1555 (1943).

(5) Production of the compound (XIV) from the compound (XII) through the compound (XIII)

The compound (XIV) is obtainable from the compound (XII) through the compound (XIII) by the method as described in Gazz. Chim. Italiana, 22, I, 242 (1892) and J. Am. Chem. Soc., 81, 94 (1959).

(6) Production of the compound (XV) from the compound (XIV)

The compound (XIV) is reduced with 5 to 15 equivalent amounts of iron powder in a solvent at a temperature of 60° to 150° C. to give the compound (XV). As the solvent, there may be employed an aliphatic carboxylic acid (e.g. acetic acid, propionic acid), if necessary, with an ester (e.g. ethyl acetate), an alcohol (e.g. methanol, ethanol, isopropanol) or water.

After completion of the reaction, the reaction mixture is subjected to ordinary post-treatment such as extraction with an organic solvent and concentration. When desired, purification by recrystallization or chromatography may be also adopted.

(7) Production of the compound (II) ($n=1$) from the compound (XV)

The compound (II) ($n=1$) is obtainable by reacting the compound (XV) with 1.0 to 2.0 equivalents of the compound (V) in the presence of 1.0 to 1.5 equivalents of a dehydrohalogenating agent in a solvent at a temperature of 0° to 80° C., preferably at 10° to 30° C. Examples of the solvent are aromatic hydrocarbons (e.g. toluene, benzene), amides (e.g. N,N-dimethylformamide), sulfur compounds (e.g. dimethylsulfoxide), nitriles (acetnitrile), water and their mixtures. As the dehydrohalogenating agent, there may be employed sodium hydride, sodium hydroxide, potassium hydroxide, etc.

After completion of the reaction, the reaction mixture is subjected to ordinary post-treatment such as addition of water, extraction with an organic solvent and concentration. When desired, purification by recrystallization or chromatography may be also adopted.

The compounds (II), (III), (IV) and (XV) are novel and can be summarized by the formula:

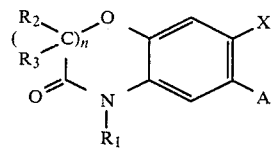

(XVI)

wherein A is an amino group or a nitro group and $R_1$, $R_2$, and $R_3$ and X are each as defined above.

Further, the compound (X) wherein X is a fluorine atom is also novel and may be representable by the formula:

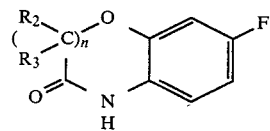

(XVII)

wherein $R_2$ and $R_3$ are each as defined above.

Typical examples for production of the starting compounds are illustratively shown in the following Examples.

EXAMPLE 4

Production of the compound (II) from the compound (IV):

Electrolytic iron (11.39 g) was suspended in 5% aqueous acetic acid solution (22 ml) and heated to 80° C. To the suspension, a solution of 5-nitro-3-(2-propynyl)-3H-benzoxazol-2-one (4.15 g) in acetic acid (20 ml) and ethyl acetate (20 ml) was dropwise added, and the resultant mixture was stirred at 70° C. for 3 hours. After being allowed to cool, water was added to the mixture, which was then extracted with ethyl acetate. The extract was washed with water and sodium bicarbonate solution, dried and concentrated to give 5-amino-3-(2-propynyl)-3H-benzoxazol-2-one (1.95 g). m.p., 102.1° C.

$^1$H-NMR (CDCl$_3$) δ ppm: 2.32 (1H, t), 3.2–3.8 (2H, broad), 4.47 (2H, d), 6.7–7.2 (3H, m).

EXAMPLE 5

Production of the compound (II) from the compound (IV):

A solution of 2-methyl-6-nitro-4-(2-propynyl)-2H-1,4-benzoxazin-3(4H)-one (5 g) in acetic acid (50 ml) and ethyl acetate (50 ml) was dropwise added to a mixture of iron powder (6 g) and 5% aqueous acetic acid (50 ml), and the resultant mixture was heated under reflux for 1 hour. After being allowed to cool, iron powder was removed by filtration and the filtrate was admixed with water. The aqueous layer was extracted with ethyl acetate, and the extract was combined with the organic layer, washed with a saturated sodium bicarbonate solution, dried and concentrated. The residue was crystallized from methanol to give 6-amino-2-methyl-4-(2-propynyl)-2H-1,4-benzoxazin-3(4H)-one (2.2 g). m.p., 158°–159° C.

$^1$H-NMR (CDCl$_3$) δ ppm: 1.5 (3H, d), 2.2 (1H, t), 3.8 (2H, m, NH$_2$).

EXAMPLE 6

Production of the compound (II) from the compound (IV):

Iron powder (1.05 g) was suspended in 5% aqueous acetic acid (2.0 ml) and heated to 80° C. To the suspension, a solution of 7-fluoro-6-nitro-4-(2-propynyl)-2H-1,4-benzoxazin-3(4H)-one (0.47 g) in acetic acid (1.9 ml) and ethyl acetate (1.9 ml) was dropwise added, and the resultant mixture was heated under reflux at 60° to 80° C. for 3 hours. After being allowed to cool, water and ethyl acetate were added to the mixture. The residue was removed by filtration, and the filtrate was extracted with ethyl acetate. The extract was washed with water and aqueous sodium bicarbonate solution, dried and concentrated to give 6-amino-7-fluoro-4-(2-propynyl)-2H-1,4-benzoxazin-3(4H)-one (0.31 g). m.p., 183°–185° C.

$^1$H-NMR (CDCl$_3$+DMSO-D$^6$) δ ppm: 2.60 (1H, t), 4.0–4.6 (2H, broad), 4.48 (2H, s), 4.58 (2H, d), 6.64 (1H, d, J=10 Hz), 6.70 (1H, d, J=6 Hz).

In the same manner as above, there are produced the compounds (III), of which typical examples are shown in Table 2.

TABLE 2

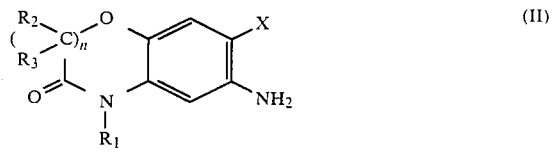

(II)

| n | $R_1$ | $R_2$ | $R_3$ | X | Physical constant |
|---|---|---|---|---|---|
| 0 | CH≡CCH$_2$— |  |  | H | m.p. 102.1° C. |
| 1 | CH$_3$ | H | H | H | m.p. 152–153.5° C. |
| 1 | C$_2$H$_5$ | H | H | H | m.p. 118–119° C. |
| 1 | C$_2$H$_5$ | H | H | F | m.p. 108.5–109.0° C. |
| 1 | C$_2$H$_5$OCH$_2$— | H | H | F | m.p. 133° C. |
| 1 | CH≡CCH$_2$— | H | H | F | m.p. 183–185° C. |
| 1 | CH≡CCH$_2$— | CH$_3$— | H | H | m.p. 158–159° C. |
| 1 | CH≡CCH$_2$— | CH$_3$— | H | F | m.p. 154.7° C. |
| 1 | CH≡CCH$_2$— | C$_2$H$_5$— | H | H | m.p. 126.5–128° C. |
| 1 | CH≡CCH$_2$— | CH$_3$— | CH$_3$ | H | m.p. 89–91° C. |
| 1 | CH≡CCH$_2$— | C$_2$H$_5$— | H | F | m.p. 121–122.5° C. |
| 1 | CH≡CCH$_2$— | CH$_3$— | CH$_3$ | F | m.p. 106–107° C. |
| 1 | CH≡CCH$_2$— | n-C$_3$H$_7$— | H | H | m.p. 124.5–125.5° C. |

TABLE 2-continued

Structure (II):

$$R_2\text{-}(C)_n\text{-}O\text{-}C_6H_2(X)(NH_2)\text{-}N(R_1)\text{-}C(=O)\text{-} \text{ (fused ring)}$$

| n | R₁ | R₂ | R₃ | X | Physical constant |
|---|---|---|---|---|---|
| 1 | (Cl)(H)C=C(Cl)(CH₂—) [Cl and CH₂ cis] | H | H | H | m.p. 97.5–99.5° C. |
| 1 | (H)(Cl)C=C(Cl)(CH₂—) | H | H | H | m.p. 137.5–138.5° C. |
| 1 | (Cl)(H)C=C(Cl)(CH₂—) | H | H | F | m.p. 133–134 C |
| 1 | (H)(Cl)C=C(Cl)(CH₂—) | H | H | F | m.p. 109.5–110.5° C. |
| 1 | CH₂=C(Cl)(CH₂—) | H | H | H | m.p. 142–143° C. |
| 1 | CH₂=C(Cl)(CH₂—) | H | H | F | m.p. 108–109° C. |
| 1 | CH≡CCH₂— | C₆H₅— (phenyl) | H | H | m.p. 168–170° C. |
| 1 | CH₃(Cl)C=CHCH₂— | H | H | H | m.p. 113–115° C. |
| 1 | CH₃(Cl)C=CHCH₂— | H | H | F | $n_D^{24.0}$ 1.5848 |
| 1 | ClCH=CHCH₂— | H | H | H | m.p. 102–104° C. |
| 1 | ClCH=CHCH₂— | H | H | F | m.p. 138–139° C. |
| 1 | Cl₂C=CHCH₂— | H | H | H | resinous |
| 1 | Cl₂C=CHCH₂— | H | H | F | m.p. 81.5–82° C. |
| 1 | BrC≡CCH₂— | H | H | H | m.p. 126.5–127.5° C. |
| 1 | BrC≡CCH₂— | H | H | F | m.p. 139.5–140.5° C. |

EXAMPLE 7

Production of the compound (IV) from the compound (III):

A suspension of sodium hydride (0.06 g) in N,N-dimethylformamide (3 ml) was cooled to 0° C. 7-Fluoro-6-nitro-2H-1,4-benzoxazin-3(4H)-one (0.57 g) was added thereto at 0° to 5° C., and the resultant mixture was stirred for 30 minutes. Propargyl bromide (0.35 g) was added to the mixture, which was gradually heated to room temperature, and the reaction was continued for 6 hours. After addition of water, the resultant mixture was extracted with ethyl acetate, and the extract was washed with water, dried and concentrated. The residue was purified by silica gel thin layer chromatography using a mixture of ethyl acetate and n-hexane (1:1) as an eluent to give 7-fluoro-6-nitro-4-(2-propynyl)-2H-1,4-benzoxazin-3(4H)-one (0.47 g). m.p., 109.1° C.

¹H-NMR (CDCl₃) δ ppm: 2.42 (1H, t), 4.75 (2H, d), 4.79 (2H, s), 6.94 (1H, d, J=10 Hz), 7.95 (1H, d, J=6 Hz).

In the same manner as above, there are produced the compound (IV), of which typical examples are shown in Table 3.

TABLE 3

(IV)

[Structure: benzene ring with $R_2R_3(C)_nO$– group at one position, $X$ at another, $NO_2$ at another, and $N(R_1)$–C(=O)– forming a ring fused to the benzene]

| n | $R_1$ | $R_2$ | $R_3$ | X | Physical constant |
|---|---|---|---|---|---|
| 0 | $CH_3$ | | | H | m.p. 120.8° C. |
| 1 | $CH_3$ | H | H | H | m.p. 189–191° C. |
| 1 | $C_2H_5$ | H | H | H | m.p. 130–131° C. |
| 1 | n-$C_3H_7$— | H | H | H | m.p. 72–73.5° C. |
| 1 | $C_2H_5$ | H | H | F | m.p. 131.6° C. |
| 1 | n-$C_3H_7$— | H | H | F | m.p. 103.7° C. |
| 1 | $CH{\equiv}CCH_2$— | H | H | F | m.p. 109.1° C. |
| 1 | $C_2H_5OCH_2$— | H | H | F | m.p. 101.6° C. |
| 1 | $CH{\equiv}CCH_2$— | $CH_3$— | H | F | resinous |
| 1 | $CH{\equiv}CCH_2$— | $C_2H_5$— | H | H | $n_D^{22.6}$ 1.5626 |
| 1 | $CH{\equiv}CCH_2$— | $CH_3$— | $CH_3$ | H | $n_D^{22.6}$ 1.5630 |
| 1 | $CH{\equiv}CCH_2$— | $C_2H_5$— | H | F | $n_D^{23.8}$ 1.5661 |
| 1 | $CH{\equiv}CCH_2$— | $CH_3$— | $CH_3$ | F | m.p. 105.3° C. |
| 1 | $CH{\equiv}CCH_2$— | n-$C_3H_7$— | H | H | m.p. 124.5–125.5° C. |
| 1 | $CH{\equiv}CCH_2$— | H | H | Cl | m.p. 157.4° C. |
| 1 | $CH{\equiv}CCH_2$— | phenyl | H | H | $n_D^{24.2}$ 1.5967 |
| 1 | ClCH=C(H)–CH(Cl)–CH$_2$— (Cl/H on one C, CH$_2$/Cl on the other) | H | H | H | $n_D^{24.2}$ 1.5819 |
| 1 | H/Cl C=C Cl/CH$_2$— | H | H | F | $n_D^{24.2}$ 1.5926 |
| 1 | Cl/H C=C Cl/CH$_2$— | H | H | H | m.p. 97.5–99.5° C. |
| 1 | H/Cl C=C Cl/CH$_2$— | H | H | F | m.p. 125–126° C. |
| 1 | $CH_2{=}C(Cl)CH_2$— | H | H | H | m.p. 110–111° C. |
| 1 | $CH_2{=}C(Cl)CH_2$— | H | H | F | m.p. 106–107° C. |
| 1 | $ClCH_2CH{=}CHCH_2$— | H | H | H | $n_D^{26.4}$ 1.6068 |
| 1 | $ClCH_2CH{=}CHCH_2$— | H | H | F | $n_D^{26.4}$ 1.5870 |
| 1 | $BrCH_2CH{=}CHCH_2$— | H | H | H | m.p. 81.5–83° C. |
| 1 | $BrCH_2CH{=}CHCH_2$— | H | H | F | m.p. 108–109° C. |
| 1 | $CH_3(Cl)C{=}CHCH_2$— | H | H | H | m.p. 117–118° C. |
| 1 | $CH_3(Cl)C{=}CHCH_2$— | H | H | F | m.p. 113–115° C. |
| 1 | $ClCH{=}CHCH_2$— | H | H | H | m.p. 103.5–105° C. |
| 1 | $ClCH{=}CHCH_2$— | H | H | F | m.p. 67–69° C. |
| 1 | $Cl_2C{=}CHCH_2$— | H | H | H | m.p. 80–82° C. |
| 1 | $Cl_2C{=}CHCH_2$— | H | H | F | m.p. 83.5–85.5° C. |
| 1 | $BrC{\equiv}CCH_2$— | H | H | H | m.p. 115.5–117° C. |
| 1 | $BrC{\equiv}CCH_2$— | H | H | F | m.p. 152–153° C. |

EXAMPLE 8

Production of the compound (III) from the compound (VIII):

A solution of 6-fluoro-2(3H)-benzoxazolone (1.0 g) in 80% aqueous sulfuric acid (6.5 g) was cooled to 0° to 5° C., and 60% nitric acid (0.8 g) was gradually added thereto at 0° to 5° C. The resultant mixture was stirred at the same temperature for 30 minutes and poured onto ice water. The precipitated crystals were collected by filtration, washed with water and dried to give 6-fluoro-5-nitro-2(3H)-benzoxazolone (1.1 g). m.p., 175.4° C.

$^1$H-NMR (CDCl$_3$+DMSO-D$^6$) δ ppm: 4.0 (1H, broad), 6.8–7.9 (3H, m).

EXAMPLE 9

Production of the compound (III) from the compound (X):

A solution of 7-fluoro-2H-1,4-benzoxazin-3(4H)-one (2.0 g) in 80% aqueous sulfuric acid (30 ml) was cooled to 0° to 5° C., and 60% nitric acid (1.6 g) was gradually added thereto at 0° to 5° C. The resultant mixture was stirred at the same temperature for 30 minutes and poured onto ice water. The precipitated crystals were collected by filtration, washed with water and dried to give 7-fluoro-6-nitro-2H-1,4-benzoxazin-3(4H)-one (2.1 g) as pale brown crystals. m.p., 205.9° C.

$^1$H-NMR (CDCl$_3$+DMSO-D$^6$) δ ppm: 3.2 (1H, broad), 4.62 (2H, s), 6.76 (1H, d, J=10 Hz), 7.6 (1H, d, J=6 Hz).

In the same manner as above, there are produced the compounds (III), of which typical examples are shown in Table 4.

TABLE 4

(III)

| n | R$_2$ | R$_3$ | X | Physical constant |
|---|-------|-------|---|-------------------|
| 0 |       |       | F | m.p. 175.4° C. |
| 1 | H     | H     | F | m.p. 205.9° C. |
| 1 | CH$_3$— | H   | F | m.p. 233.6° C. |
| 1 | C$_2$H$_5$— | H | H | m.p. 138–139° C. |
| 1 | CH$_3$— | CH$_3$— | H | m.p. 162° C. |
| 1 | C$_2$H$_5$— | H | F | m.p. 149–151° C. |
| 1 | CH$_3$— | CH$_3$— | F | m.p. 134.5–136° C. |
| 1 | CH$_3$CH$_2$CH$_2$— | H | H | m.p. 165–167° C. |
| 1 | (CH$_3$)$_2$CH— | H | H | m.p. 120° C. |
| 1 | CH$_3$CH$_2$CH$_2$— | H | F | m.p. 164–165° C. |
| 1 | phenyl | H | H | m.p. 148–150° C. |
| 1 | phenyl | H | F | m.p. 135.5–137° C. |

EXAMPLE 10

Production of the compound (X) from the compound (IX):

Iron powder (36.42 g) was suspended in 5% aqueous acetic acid (69 ml) and heated to 80° C. To the suspension, a solution of ethyl 5-fluoro-2-nitrophenoxyacetate (15.86 g) in acetic acid (65 ml) and ethyl acetate (65 ml) was dropwise added, and the resultant mixture was heated at 60° to 80° C. under reflux for 3 hours. After removal of residue by filtration, the filtrate was extracted with ethyl acetate. The extract was washed with water and sodium bicarbonate solution, dried and concentrated to give 7-fluoro-2H-1,4-benzoxazin-3(4H)-one (6.82 g). m.p., 186.7° C.

$^1$H-NMR (CDCl$_3$+DMSO-D$^6$) δ ppm: 4.2 (1H, broad), 4.51 (2H, s), 6.5–7.0 (3H, m).

In the same manner as above, there are produced the compound (X), of which typical examples are shown in Table 5.

TABLE 5

(X)

| R$_2$ | R$_3$ | Physical constant |
|-------|-------|-------------------|
| H | H | m.p. 186.7° C. |
| CH$_3$ | H | m.p. 151.3° C. |
| C$_2$H$_5$ | H | m.p. 121–123° C. |
| CH$_3$ | CH$_3$ | m.p. 133–134° C. |
| n-C$_3$H$_7$ | H | m.p. 99–101° C. |
| phenyl | H | m.p. 153–155° C. |

EXAMPLE 11

Production of the compound (XV) from the compound (XIV):

A mixture of iron powder (2.4 g) in acetic acid (1 g) and water (20 ml) was refluxed, and a solution of methyl 2,4-dinitrophenoxacetate (2.24 g) in ethanol (20 ml) and ethyl acetate (10 ml) was dropwise added thereto. The resultant mixture was stirred for 1 hour and concentrated under reduced pressure to evaporate ethanol. To the residue, water and ethyl acetate was added, and extraction was carried out. The organic layer was dried and concentrated, and the residue was combined with ether. The precipitated crystals were collected by filtration to give 6-amino-2H-1,4-benzoxazin-3(4H)-one (1.1 g).

$^1$H-NMR (DMSO-d$^6$) δ ppm: 4.3 (2H, m, NH$_2$), 4.4 (2H, s), 6.25 (1H, d, d), 6.3 (1H, d), 6.7 (1H, d), 10.3 (1H, m, $$-\underset{\underset{O}{\|}}{C}NH).$$

EXAMPLE 12

Production of the compound (II) from the compound (XV):

Sodium hydride (0.08 g) was suspended in dry N,N-dimethylformamide (3 ml), and the suspension was cooled to 0° C. While stirring, 6-amino-2H-1,4-benzoxazin-3(4H)-one (0.5 g) was portionwise added to the suspension at 0° C., and the resultant mixture was stirred at the same temperature for 30 minutes. To the mixture, propargyl chloride (0.25 g) was dropwise added, and the mixture was stirred at room temperature for 6 hours. Water was added to the reaction mixture, which was then extracted with ethyl acetate. The extract was washed with water, dried and concentrated to give 6-amino-4-(2-propynyl)-2H-1,4-benzoxazin-3(4H)-one (0.36 g). m.p., 260.1° C.

On the practical usage of the tetrahydrophthalimides (I), they may be applied in any preparation form such as emulsifiable concentrates, wettable powders, suspensions, granules, etc. in combination with conventional solid or liquid carriers or diluents as well as surface active agents of auxiliary agents.

The content of the tetrahydrophthalimides (I) as the active ingredient in such formulation form is usually within a range of 0.05 to 90% by weight, preferably 0.1 to 80% by weight.

Examples of the solid carrier or diluent are fine powders or granules of kaolin clay, attapulgite clay, bentonite, terra alba, pyrophyllite, talc, diatomaceous earth, calcite, walnut powders, urea, ammonium sulfate and synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, N,N-dimethylformamide, acetonitrile, water, etc.

The surface active agent used for emulsification, dispersion or spreading may be any of the anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl celluloe), PAP (isopropyl acid phosphate), etc.

Practical embodiments of the herbicidal composition according to the invention are illustratively shown in the following examples wherein parts are by weight. The compound number of the active ingredient corresponds to the one in Table 1.

FORMULATION EXAMPLE 1

Fifty parts of Compound No. 1, 15 or 20, 3 parts of calcium ligninsulfonate, 2 parts of sodium laurylsulfate and 45 parts of synthetic hydrous silicate are well mixed while being powdered to obtain a wettable powder.

FORMULATION EXAMPLE 2

Five parts of Compound No. 5, 9, 13 or 21, 14 parts of polyoxyethylenestyrylphenyl ether, 6 parts of calcium dodecylbenzenesulfonate, 30 parts of xylene and 45 parts of isophorone are well mixed while being powdered to obtain an emulsifiable concentrate.

FORMULATION EXAMPLE 3

Two parts of Compound No. 4, 10 or 20, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

FORMULATION EXAMPLE 4

Twenty-five parts of Compound No. 2, 15 or 22 is mixed with 3 parts of polyoxyethylene sorbitan monooleate, 3 parts of carboxymethyl cellulose and 69 parts of water and pulverized until the particle size of the mixture becomes less than 5 microns to obtain a suspension.

FORMULATION EXAMPLE 5

Five parts of Compound No. 2, 5, 9, 13, 15, 16, 20, 21 or 25, 14 parts of polyoxyethylenestyrylphenyl ether, 6 parts of calcium dodecylbenzenesulfonate, 30 parts of xylene and 45 parts of N,N-dimethylformamide are well mixed while being powdered to obtain an emulsifiable concentrate.

FORMULATION EXAMPLE 6

Eighty parts of Compound No. 2, 16, 22 or 50, 3 parts of calcium ligninsulfonate, 2 parts of sodium laurylsulfate and 15 parts of synthetic hydrous silicate are well mixed while being powdered to obtain a wettable powder.

FORMULATION EXAMPLE 7

0.1 Part of Compound No. 10 or 15, 0.9 part of synthetic hydrous silicate, 2 parts of calcium ligninsulfonate, 30 parts of bentonite and 67 parts of kaolin clay are well mixed while being powdered. The mixture is then kneaded with water, granulated and dried to obtain granules.

The tetrahydrophthalimides (I) thus formulated in any suitable formulation form are useful for the pre-emergence or post-emergence control of undesired weeds by soil or foliar treatment as well as flood fallowing treatment. These treatments include the application to the soil surface prior to or after the transplanting or the incorporation into the soil. The foliar treatment may be effected by spraying the herbicidal composition containing the tetrahydrophthalimides (I) over the top of the plants. It may also be applied directly to the weeds if care is taken to keep the chemical off the crop foliage.

The tetrahydrophthalimides (I) of the invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

Furthermore, the tetrahydrophthalimides (I) can be used as herbicides applicable to agricultural plowed field as well as paddy field. They are also useful as herbicides to be employed for orchard, pasture land, lawn, forest, non-agricultural field, etc.

The dosage rate of the tetrahydrophthalimides (I) may vary on prevailing weather conditions, formulation used, prevailing season, mode of application, soil involved, crop and weed species, etc. Generally, however, the dosage rate is from 0.02 to 100 grams, preferably from 0.05 to 50 grams, of the active ingredient per are. The herbicidal composition of the invention formulated in the form of an emulsifiable concentrate, a wettable powder or a suspension may ordinarily be employed by diluting it with water at a volume of 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition formulated in the form of granules may be normally applied as such without dilution.

The biological data of the tetrahydrophthalimides (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, in which the numeral "0" indicates no material difference is seen in comparison with the untreated plant and the numeral "5" indicates the complete inhibition or death of the test plants.

The compounds shown in Table 6 below were used for comparison.

TABLE 6

| Compound No. | Chemical structure | Remarks |
|---|---|---|
| A | (structure) | U.S. Pat. No. 3,878,224 |
| B | (structure) | Commercially available herbicide; "chloronitrofen" |
| C | (structure) | Commercially available herbicide; "metabenzthiazuron" |
| D | (structure) | Commercially available herbicide; "linuron" |

TEST EXAMPLE 1

Cylindrical plastic pots (diameter, 10 cm; height, 10 cm) were filled with upland field soil, and the seeds of Japanese millet, tall morningglory and velvetleaf were sowed therein and covered with soil. A designed amount of the test compound formulated in an emulsifiable concentrate according to Formulation Example 2 or 5 was diluted with water, and the dilution was sprayed onto the soil surface by means of a small hand sprayer at a spray volume of 10 liters per are. The test plants were further grown in a greenhouse for 20 days, and the herbicidal activity was examined.

The results are shown in Table 7.

TABLE 7

| Compound No. | Dosage (g/are) | Herbicidal activity | | |
|---|---|---|---|---|
| | | Japanese millet | Tall morning-glory | Velvet-leaf |
| 1 | 20 | 5 | 5 | 5 |
| | 10 | 4 | 5 | 5 |
| 2 | 20 | 5 | 5 | 5 |
| | 10 | 5 | 5 | 5 |
| 3 | 20 | 5 | 5 | 5 |
| | 10 | 4 | 5 | 5 |
| 4 | 20 | 5 | 5 | 5 |
| 5 | 20 | 5 | 5 | 5 |

TABLE 7-continued

| Compound No. | Dosage (g/are) | Herbicidal activity | | |
|---|---|---|---|---|
| | | Japanese millet | Tall morning-glory | Velvet-leaf |
| 6 | 20 | 5 | 5 | 5 |
| 7 | 20 | 5 | 5 | 5 |
| 8 | 20 | 5 | 5 | 5 |
| | 10 | 4 | 4 | 5 |
| 9 | 20 | 5 | 5 | 5 |
| | 10 | 4 | 4 | 5 |
| 10 | 20 | 5 | 5 | 5 |
| | 10 | 5 | 5 | 5 |
| 11 | 20 | 5 | 5 | 5 |
| 12 | 20 | 5 | 5 | 5 |
| 13 | 20 | 5 | 5 | 5 |
| 14 | 20 | 5 | 5 | 5 |
| | 10 | 4 | 5 | 5 |
| 15 | 10 | 5 | 5 | 5 |
| | 5 | 5 | 5 | 5 |
| 16 | 10 | 4 | 5 | 5 |
| | 5 | 4 | 5 | 5 |
| 17 | 20 | 5 | 5 | 5 |
| 18 | 20 | 5 | 5 | 5 |
| 19 | 20 | 5 | 5 | 5 |
| 20 | 10 | 5 | 5 | 5 |
| | 5 | 5 | 5 | 5 |
| 21 | 20 | 5 | 5 | 5 |
| | 10 | 5 | 5 | 5 |
| 22 | 10 | 5 | 5 | 5 |
| | 5 | 5 | 5 | 5 |
| 23 | 20 | 5 | 5 | 5 |
| | 10 | 5 | 5 | 5 |
| 24 | 20 | 5 | 5 | 5 |
| | 10 | 5 | 5 | 5 |
| 25 | 10 | 5 | 5 | 5 |
| | 5 | 5 | 5 | 5 |
| 27 | 20 | 5 | 4 | 5 |
| 28 | 20 | 4 | 4 | 5 |
| 29 | 20 | 4 | 4 | 5 |
| 33 | 20 | 5 | 5 | 5 |
| 36 | 20 | 3 | 5 | 5 |
| 37 | 20 | — | 5 | 5 |
| 39 | 20 | 4 | 5 | 5 |
| 40 | 20 | 4 | 5 | 5 |
| 43 | 20 | 4 | 4 | 5 |
| 44 | 20 | 4 | 4 | 5 |
| 45 | 20 | 4 | 4 | 5 |
| 46 | 20 | 5 | 5 | 5 |
| 48 | 20 | 5 | 5 | 5 |
| | 10 | — | 5 | 5 |
| 49 | 20 | 5 | 5 | 5 |
| | 10 | 5 | 5 | 5 |
| A | 20 | 2 | 0 | 3 |
| | 10 | 1 | 0 | 1 |
| B | 20 | 1 | 1 | 2 |
| | 10 | 0 | 0 | 0 |

TEST EXAMPLE 2

Cylindrical plastic pots (diameter, 10 cm; height, 10 cm) were filled with upland field soil, and the seeds of Japanese millet, radish and velvetleaf were sowed therein and cultivated in a greenhouse for 10 days. A designed amount of the test compound formulated in an emulsifiable concentrate according to Formulation Example 2 or 5 was diluted with water containing a spreading agent, and the dilution was sprayed over the foliage of the test plants by means of a small hand sprayer at a spray volume of 10 liters per are. The test plants were further grown in the greenhouse for 20 days, and the herbicidal activity was examined.

The results are shown in Table 8.

TABLE 8

| Compound No. | Dosage (g/are) | Herbicidal activity | | |
|---|---|---|---|---|
| | | Japanese millet | Radish | Velvetleaf |
| 1 | 5 | 4 | 5 | 5 |
| 2 | 5 | 5 | 5 | 5 |
| | 2.5 | 4 | 5 | 5 |
| 3 | 5 | 4 | 4 | 5 |
| 4 | 5 | 4 | 4 | 5 |
| 5 | 5 | 4 | 4 | 5 |
| 6 | 5 | 4 | 5 | 5 |
| 7 | 5 | 4 | 5 | 5 |
| 8 | 5 | 5 | 4 | 5 |
| 9 | 5 | 4 | 5 | 5 |
| | 2.5 | — | 5 | 5 |
| 10 | 5 | 5 | 5 | 5 |
| | 2.5 | 4 | 5 | 5 |
| 11 | 5 | 4 | 5 | 5 |
| 12 | 5 | — | 5 | 5 |
| 13 | 5 | 4 | 5 | 5 |
| 14 | 5 | 5 | 5 | 5 |
| | 2.5 | 4 | 5 | 5 |
| 15 | 5 | 5 | 5 | 5 |
| | 2.5 | 4 | 5 | 5 |
| 16 | 5 | 5 | 5 | 5 |
| | 2.5 | 4 | 5 | 5 |
| 17 | 5 | 5 | 5 | 5 |
| | 2.5 | 4 | 5 | 5 |
| 18 | 5 | 5 | 5 | 5 |
| 19 | 5 | 5 | 5 | 5 |
| 20 | 5 | 5 | 5 | 5 |
| | 2.5 | 5 | 5 | 5 |
| 21 | 5 | 4 | 5 | 5 |
| | 2.5 | 4 | 5 | 5 |
| 22 | 5 | 5 | 5 | 5 |
| | 2.5 | 5 | 5 | 5 |
| 23 | 5 | 5 | 5 | 5 |
| | 2.5 | 4 | 5 | 5 |
| 24 | 5 | 5 | 5 | 5 |
| | 2.5 | 4 | 5 | 5 |
| 25 | 5 | 5 | 5 | 5 |
| | 2.5 | 5 | 5 | 5 |
| 26 | 5 | — | 5 | 5 |
| 27 | 5 | — | 5 | 5 |
| 28 | 5 | — | 5 | 5 |
| 29 | 5 | — | 5 | 5 |
| 31 | 5 | — | 3 | 5 |
| 33 | 5 | 5 | 5 | 5 |
| 34 | 5 | — | 4 | 5 |
| 35 | 5 | — | 4 | 5 |
| 36 | 5 | — | 5 | 5 |
| 37 | 5 | 4 | 5 | 5 |
| 38 | 5 | — | 5 | 5 |
| 39 | 5 | 5 | 5 | 5 |
| 40 | 5 | 5 | 5 | 5 |
| 41 | 5 | — | 4 | 4 |
| 42 | 5 | — | 3 | 5 |
| 43 | 5 | 5 | 5 | 5 |
| 44 | 5 | 4 | 5 | 5 |
| 46 | 5 | 5 | 5 | 5 |
| 48 | 5 | 5 | 5 | 5 |
| 49 | 5 | 5 | 5 | 5 |
| | 2.5 | 4 | 5 | 5 |
| 50 | 5 | — | 3 | 5 |
| A | 5 | 2 | 2 | 3 |
| | 2.5 | 0 | 0 | 0 |
| B | 5 | 2 | 0 | 3 |
| | 2.5 | 0 | 0 | 1 |

TEST EXAMPLE 3

Cylindrical plastic pots (diameter, 8 cm; height, 12 cm) were filled with paddy field soil, and the seeds of barnyardgrass (*Echinochloa oryzicola*) and broad-leaved weeds (e.g. common falsepimpernel, indian toothcup, waterwort) were sowed in 1 to 2 cm depth. Water was poured therein to make a flooded condition, and rice seedlings of the 2-leaf stage were transplanted therein and grown in a greenhouse. Six days (at that time the weeds began to germinate) thereafter, a designed amount of the test compound formulated in an emulsifiable concentrate according to Formulation Example 2 or 5 and diluted with water (5 ml) was applied to the pots by perfusion. The test plants were grown for further 20 days in the greenhouse, and the herbicidal activity was examined.

The results are shown in Table 9.

TABLE 9

| Compound No. | Dosage (g/are) | Herbicidal activity | | |
|---|---|---|---|---|
| | | Rice plant | Barnyard-grass | Broad-leaved weed |
| 2 | 10 | — | 5 | 5 |
| | 5 | 1 | 5 | 5 |
| 3 | 10 | 1 | 4 | 5 |
| 4 | 10 | 0 | 4 | 5 |
| 5 | 10 | 0 | 4 | 5 |
| 7 | 10 | 1 | 4 | 5 |
| 9 | 10 | 1 | 4 | 5 |
| 10 | 10 | 0 | 5 | 5 |
| | 5 | 0 | 4 | 5 |
| 15 | 10 | 2 | 5 | 5 |
| | 5 | 1 | 5 | 5 |
| 20 | 5 | 2 | 5 | 5 |
| 21 | 10 | 1 | 5 | 5 |
| 24 | 10 | 0 | 5 | 5 |
| 31 | 10 | 0 | 4 | 5 |
| A | 10 | 1 | 2 | 5 |
| | 5 | 0 | 0 | 2 |

TEST EXAMPLE 4

Vats (33 cm × 23 cm × 11 cm) were filled with upland field soil, and the seeds of soybean, peanut, corn, common cocklebur, tall morningglory, velvetleaf, redroot pigweed, black nightshade, barnyardgrass and green foxtail were sowed therein to 1 to 2 cm depth. A designed amount of the test compound formulated in an emulsifiable concentrate according to Formulation Example 2 or 5 was diluted with water, and the dilution was sprayed onto the soil surface by means of a small hand sprayer at a spray volume of 10 liters per are. The test plants were further grown in a greenhouse for 20 days, and the herbicidal activity was examined.

The results are shown in Table 10.

TABLE 10

| Compound No. | Dosage (g/are) | Herbicidal activity | | | | | | | | | |
|---|---|---|---|---|---|---|---|---|---|---|---|
| | | Soybean | Peanut | Corn | Common cocklebur | Tall morning-glory | Velvet-leaf | Redroot pigweed | Black night-shade | Barn-yard-grass | Green fox-tail |
| 1 | 5 | 1 | 0 | 2 | 4 | 5 | 5 | 5 | 5 | 5 | 4 |
| 2 | 5 | 2 | — | 2 | 5 | 5 | 5 | 5 | 5 | 5 | 5 |
| | 2.5 | 2 | — | 0 | 3 | 4 | 5 | 5 | 5 | 3 | 4 |
| 3 | 5 | 0 | 0 | 2 | — | 4 | 5 | 5 | 4 | 4 | 4 |
| 8 | 5 | 0 | 0 | 1 | 4 | — | 4 | 5 | 4 | — | 4 |
| 9 | 5 | 0 | 0 | — | — | 5 | 5 | 5 | 5 | 4 | 4 |

TABLE 10-continued

| Compound No. | Dosage (g/are) | Herbicidal activity | | | | | | | | |
|---|---|---|---|---|---|---|---|---|---|---|
| | | Soybean | Peanut | Corn | Common cocklebur | Tall morning-glory | Velvet-leaf | Redroot pigweed | Black night-shade | Barn-yard-grass | Green fox-tail |
| 10 | 5 | 0 | 0 | 1 | — | 4 | 5 | 5 | 5 | 4 | 3 |
| 14 | 5 | 0 | 0 | — | 5 | 5 | 5 | 5 | 5 | 4 | 4 |
| | 2.5 | 0 | 0 | — | 4 | 5 | 5 | 5 | 5 | — | — |
| 15 | 2.5 | 0 | 0 | 2 | 5 | 5 | 5 | 5 | 5 | 4 | 5 |
| | 1.25 | 0 | 0 | 1 | — | 4 | 5 | 5 | 4 | — | 4 |
| 16 | 2.5 | 0 | 0 | 1 | 4 | 5 | 5 | 5 | 5 | 4 | — |
| | 1.25 | 0 | 0 | 0 | — | 4 | 5 | 5 | 4 | — | — |
| 20 | 2.5 | 0 | 0 | 2 | 5 | 5 | 5 | 5 | 5 | 5 | 5 |
| | 1.25 | 0 | 0 | 1 | 4 | 5 | 5 | 5 | 5 | 4 | 5 |
| 21 | 5 | 0 | 0 | — | 5 | 5 | 5 | 5 | 5 | 5 | 5 |
| | 2.5 | 0 | 0 | — | 4 | 4 | 5 | 5 | 5 | 4 | 5 |
| 22 | 2.5 | 0 | 0 | — | 5 | 5 | 5 | 5 | 5 | 4 | 5 |
| | 1.25 | 0 | 0 | — | — | 4 | 5 | 5 | 5 | — | 4 |
| 23 | 5 | 1 | 0 | 1 | 5 | 5 | 5 | 5 | 5 | 5 | 5 |
| | 2.5 | 0 | 0 | 1 | — | 5 | 5 | 5 | 5 | 4 | 4 |
| 24 | 5 | 0 | 0 | — | 5 | 5 | 5 | 5 | 5 | 5 | 5 |
| | 2.5 | 0 | 0 | — | 4 | 4 | 5 | 5 | 5 | 4 | 5 |
| 25 | 2.5 | 0 | 0 | 1 | 4 | 5 | 5 | 5 | 5 | 4 | 5 |
| | 1.25 | 0 | 0 | 1 | — | 4 | 5 | 5 | 4 | — | 4 |
| 48 | 5 | 0 | 0 | — | 5 | 5 | 5 | 5 | 5 | — | 5 |
| 49 | 5 | 1 | 1 | — | 5 | 5 | 5 | 5 | 5 | 5 | 5 |
| | 2.5 | 0 | 0 | — | 4 | 5 | 5 | 5 | 5 | 4 | 4 |
| A | 5 | 0 | 0 | 0 | 0 | 0 | 2 | 2 | 1 | 1 | 1 |
| | 2.5 | 0 | 0 | 0 | 0 | 0 | 0 | 0 | 0 | 0 | 0 |
| B | 5 | 0 | 0 | 0 | 0 | 0 | 1 | 1 | 1 | 1 | 0 |
| | 2.5 | 0 | 0 | 0 | 0 | 0 | 0 | 0 | 0 | 0 | 0 |

TEST EXAMPLE 5

Vats (33 cm×23 cm×11 cm) were filled with upland field soil, and the seeds of wheat, barley, catchweed bedstraw, persian speedwell, common chickweed, common lambsquarters, pale smartweed, wild buckwheat and annual bluegrass were sowed therein to 1 to 2 cm depth. A designed amount of the test compound formulated in an emulsifiable concentrate according to Formulation Example 2 or 5 was diluted with water, and the dilution was sprayed onto the soil surface by means of a small hand sprayer at a spray volume of 10 liters per are. The test plants were further grown in a greenhouse for 27 days, and the herbicidal activity was examined. The results are shown in Table 11.

TABLE 11

| Compound No. | Dosage (g/are) | Herbicidal activity | | | | | | | | |
|---|---|---|---|---|---|---|---|---|---|---|
| | | Wheat | Barley | Catchweed bedstraw | Persian speed-well | Common chick-weed | common lambs-quarters | Pale smart-weed | Wild buck-wheat | Annual blue-grass |
| 2 | 2.5 | 1 | 1 | 5 | 5 | 5 | 5 | 5 | 5 | 4 |
| 4 | 2.5 | 1 | 1 | 4 | 5 | 5 | 5 | 5 | 5 | 4 |
| 5 | 2.5 | 1 | 1 | 4 | 5 | 4 | 5 | 4 | 5 | — |
| 9 | 2.5 | 1 | 1 | 5 | 5 | 5 | 5 | 5 | 5 | 4 |
| | 1.25 | 0 | 1 | — | 5 | — | 5 | 4 | 5 | — |
| 14 | 2.5 | 1 | 1 | 5 | 5 | 5 | 5 | 5 | 5 | 4 |
| | 1.25 | 0 | 0 | — | 5 | 4 | 5 | 5 | 5 | — |
| 15 | 1.25 | 0 | 0 | 5 | 5 | 5 | 5 | 5 | 5 | 4 |
| | 0.63 | 0 | 0 | 4 | 5 | 5 | 5 | — | 5 | — |
| 16 | 1.25 | 0 | 0 | 5 | 5 | 5 | 5 | 5 | 5 | — |
| | 0.63 | 0 | 0 | 4 | 5 | 5 | 5 | 5 | 5 | — |
| 20 | 1.25 | 2 | 1 | 5 | 5 | 5 | 5 | 5 | 5 | 5 |
| | 0.63 | 1 | 1 | 5 | 5 | 5 | 5 | 5 | 5 | — |
| 21 | 2.5 | — | 1 | 5 | 5 | 5 | 5 | 5 | 5 | 5 |
| | 1.25 | 0 | 1 | — | 5 | — | 5 | 5 | 5 | — |
| 20 | 1.25 | 0 | 1 | 5 | 5 | 5 | 5 | 5 | 5 | 4 |
| | 0.63 | 0 | 0 | — | 5 | 5 | 5 | 4 | 4 | — |
| 23 | 2.5 | 1 | — | 5 | 5 | 5 | 5 | 5 | 5 | 5 |
| | 1.25 | 0 | — | — | 5 | 4 | 5 | 5 | 4 | — |
| 24 | 2.5 | — | 1 | 5 | 5 | 5 | 5 | 5 | 5 | 4 |
| | 1.25 | 0 | 0 | — | 5 | 4 | 5 | 5 | 5 | — |
| 25 | 1.25 | 0 | 0 | 5 | 5 | 5 | 5 | 5 | 5 | 4 |
| | 0.63 | 0 | 0 | — | 5 | 5 | 5 | 5 | 5 | — |
| A | 2.5 | 0 | 0 | 0 | 0 | 0 | 1 | 0 | 0 | 0 |
| | 1.25 | 0 | 0 | 0 | 0 | 0 | 0 | 0 | 0 | 0 |
| B | 2.5 | 0 | 0 | 0 | 0 | 0 | 0 | 0 | 0 | 0 |
| | 1.25 | 0 | 0 | 0 | 0 | 0 | 0 | 0 | 0 | 0 |

TEST EXAMPLE 6

Vats (33 cm×23 cm×11 cm) were filled with upland field soil, and the seeds of corn, wheat, common cocklebur, velvetleaf, black nightshade, tall morningglory, common lambsquarters and green foxtail were sowed therein and cultivated for 18 days in a greenhouse. A designed amount of the test compound formulated in an emulsifiable concentrate according to Formulation Example 2 or 5 was diluted with water containing a spreading agent, and the dilution was sprayed over the foliage of the test plants by means of a small hand sprayer at a spray volume of 5 liters per are. The test plants were further grown in the greenhouse for 20 days, and the herbicidal activity was examined. At the time of the application, the test plants were generally at the 1 to 4 leaf stage and in 2 to 12 cm height, although growing stage of the test plants varied depending on their species.

The results are shown in Table 12.

test plants were further grown in a greenhouse for 21 days, and the herbicidal activity was examined.

The results are shown in Table 13.

TABLE 13

| Compound No. | Dosage (g/are) | Herbicidal activity | | | | | | | |
|---|---|---|---|---|---|---|---|---|---|
| | | Soybean | Peanut | Sicklepod | Hemp sesbania | Velvet-leaf | Prickly sida | Jimson-weed | Large crab-grass |
| 15 | 2.5 | 0 | 0 | 4 | 5 | 5 | 5 | 5 | 4 |
| | 1.25 | 0 | 0 | — | 4 | 5 | 5 | 4 | — |
| 20 | 2.5 | 0 | 0 | 5 | 5 | 5 | 5 | 5 | 5 |
| | 1.25 | 0 | 0 | 5 | 5 | 5 | 5 | 4 | 4 |
| 22 | 2.5 | 0 | 0 | 5 | 5 | 5 | 5 | 5 | 5 |
| | 1.25 | 0 | 0 | 4 | 5 | 5 | 5 | 4 | — |
| D | 2.5 | 0 | 0 | 0 | 0 | 0 | 1 | 1 | 0 |
| | 1.25 | 0 | 0 | 0 | 0 | 0 | 0 | 0 | 0 |

TEST EXAMPLE 8

Seeds of wheat, catchweed bedstraw, common chickweed, persian speedwell and common lambsquarters were sowed in the field as previously laid up in ridges and divided into plots of 4 m². A designed amount of the test compound formulated into a wettable powder according to Formulation Example 1 was diluted with water and sprayed onto the soil surface by means of a small hand sprayer at a spray volume of 7.5 liters per are. The application was made with three replications. After cultivation for 39 days, the herbicidal activity on the weeds as well as the phytotoxicity on wheat were evaluated as follows: the serial parts of the test plants were cut off and weighed (fresh weight) and growth inhibition rate was calculated based thereon according to the following equation:

TABLE 12

| Compound No. | Dosage (g/are) | Corn | Wheat | Common cock-lebur | Velvet-leaf | Black night-shade | Tall morning-glory | Common lambs-quarters | Green foxtail |
|---|---|---|---|---|---|---|---|---|---|
| 1 | 0.3 | — | — | 5 | 5 | 5 | 5 | 5 | 4 |
| | 0.1 | 2 | 1 | — | 4 | 5 | 5 | 5 | — |
| 2 | 0.3 | 1 | 1 | 5 | 5 | 5 | 5 | 5 | 4 |
| | 0.1 | 0 | 0 | — | 5 | 5 | 5 | 5 | — |
| 5 | 0.3 | — | — | 4 | 5 | 5 | 5 | 5 | — |
| | 0.1 | 1 | 1 | — | 4 | 4 | 4 | 5 | — |
| 10 | 0.3 | — | — | 5 | 5 | 5 | 5 | 5 | 4 |
| | 0.1 | 1 | 1 | 5 | 5 | 5 | 5 | 5 | — |
| 14 | 0.3 | — | — | 5 | 5 | 5 | 5 | 5 | 4 |
| | 0.1 | 1 | 1 | 5 | 5 | 5 | 5 | 5 | — |
| 15 | 0.3 | 1 | — | 5 | 5 | 5 | 5 | 5 | 4 |
| | 0.1 | 0 | 1 | 5 | 5 | 5 | 5 | 5 | — |
| 16 | 0.3 | 1 | — | 5 | 5 | 5 | 5 | 5 | — |
| | 0.1 | 0 | 1 | 5 | 5 | 5 | 5 | 5 | — |
| 20 | 0.3 | — | — | 5 | 5 | 5 | 5 | 5 | 4 |
| | 0.1 | 1 | 1 | 5 | 5 | 5 | 5 | 5 | — |
| 21 | 0.3 | — | — | 5 | 5 | 5 | 5 | 5 | 4 |
| | 0.1 | 0 | 0 | — | 5 | 5 | 5 | 5 | — |
| 22 | 0.3 | — | — | 5 | 5 | 5 | 5 | 5 | 4 |
| | 0.1 | 0 | 1 | 5 | 5 | 5 | 5 | 5 | — |
| 23 | 0.3 | 1 | 2 | 5 | 5 | 5 | 5 | 5 | 4 |
| | 0.1 | 0 | 0 | 5 | 5 | 5 | — | 5 | — |
| 24 | 0.3 | 1 | 2 | 5 | 5 | 5 | 5 | 5 | 4 |
| | 0.1 | 1 | 1 | 5 | 5 | — | 5 | 5 | — |
| 25 | 0.3 | 1 | — | 5 | 5 | 5 | 5 | 5 | 4 |
| | 0.1 | 1 | 1 | 5 | 5 | 5 | 5 | 5 | — |
| A | 0.3 | 0 | 0 | 0 | 0 | 0 | 0 | 0 | 0 |
| | | 0 | 0 | 0 | 0 | 0 | 0 | 0 | 0 |
| B | 0.3 | 0 | 0 | 0 | 1 | 0 | 0 | 1 | 0 |
| | | 0 | 0 | 0 | 0 | 0 | 0 | 0 | 0 |

TEST EXAMPLE 7

Vats (33 cm × 23 cm × 11 cm) were filled with upland field soil, and the seeds of soybean, peanut, sicklepod, hemp sesbania, velvetleaf, prickly sida, jimsonweed and large crabgrass were sowed therein to 1 to 2 cm depth. A designed amount of the test compound formulated in an emulsifiable concentrate according to Formulation Example 2 or 5 was diluted with water, and the dilution was sprayed onto the soil surface by means of a small hand sprayer at a spray volume of 10 liters per are. The $$\text{Growth inhibition rate (\%)} = \left(1 - \frac{\text{Fresh weight of test plants in treated plot}}{\text{Fresh weight of test plants in untreated plot}}\right) \times 100$$

The results are shown in Table 14.

TABLE 14

| Compound No. | Dosage (g/are) | Wheat | Catchweed bedstraw | Common chickweed | Persian speedwell | Common lambsquarters |
|---|---|---|---|---|---|---|
| 15 | 2 | 8 | 95 | 95 | 100 | 95 |
|  | 1 | 2 | 82 | 87 | 98 | 92 |
| 16 | 4 | 5 | 97 | 97 | 100 | 100 |
|  | 2 | 1 | 89 | 89 | 100 | 95 |
| 20 | 2 | 9 | 98 | 100 | 100 | 100 |
|  | 1 | 4 | 93 | 98 | 100 | 95 |
| 25 | 2 | 8 | 97 | 100 | 100 | 100 |
|  | 1 | 3 | 91 | 93 | 97 | 94 |
| C | 20 | 2 | 27 | 97 | 87 | 63 |

TEST EXAMPLE 9

Seeds of soybean, peanut, redroot pigweed, velvetleaf, black nightshade and prickly side were sowed in the field as previously laid up in ridges and divided into plots of 3 m². A designed amount of the test compound formulated into an emulsifiable concentrate according to Formulation Example 2 or 5 was diluted with water and sprayed onto the soil surface by means of a small hand sprayer at a spray volume of 10 liters per are. The application was made with two replications. After cultivation for 40 days, the growth inhibition rate of the test plants was measured in the same manner as in Test Example 8.

The results are shown in Table 15.

TABLE 15

| Compound No. | Dosage (g/are) | Growth inhibition rate (%) | | | | |
|---|---|---|---|---|---|---|
|  |  | Soybean | Peanut | Redroot pigweed | Velvetleaf | Black nightshade | Prickly sida |
| 15 | 2 | 3 | 7 | 100 | 95 | 100 | 100 |
|  | 1 | 0 | 0 | 100 | 75 | 100 | 100 |
|  | 0.5 | 0 | 0 | 90 | 26 | 93 | 65 |
| 20 | 2 | 3 | 8 | 100 | 100 | 100 | 100 |
|  | 1 | 0 | 0 | 100 | 100 | 100 | 100 |
|  | 0.5 | 0 | 0 | 96 | 78 | 100 | 85 |
| D | 2 | 0 | 0 | 0 | 0 | 0 | 0 |
|  | 1 | 0 | 0 | 0 | 0 | 0 | 0 |
|  | 0.5 | 0 | 0 | 0 | 0 | 0 | 0 |

What is claimed is:

1. A compound of the formula:

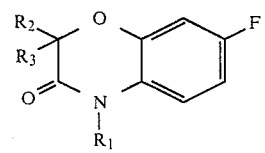

wherein $R_1$ is a hydrogen atom, and $R_2$ and $R_3$ are, the same or different, each a hydrogen atom, a halogen atom, a $C_1$–$C_3$ alkyl group or a phenyl group.

2. The compound according to claim 1 wherein $R_2$ and $R_3$ are each a hydrogen atom.

3. The compound according to claim 1 wherein $R_2$ is a hydrogen atom or a methyl group, and $R_3$ is a hydrogen atom.

* * * * *